Figure 1:
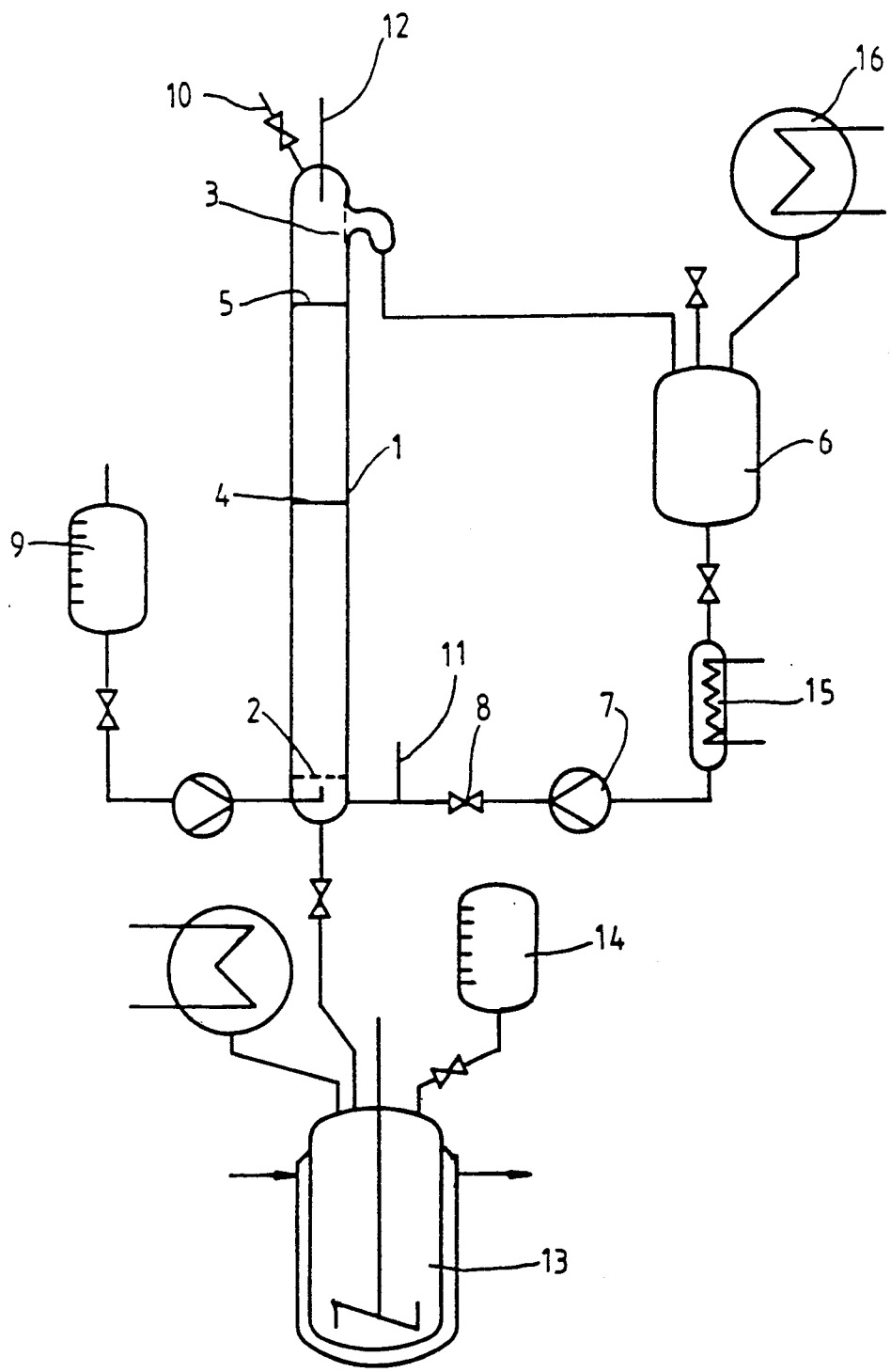

United States Patent [19]

Rosen et al.

[11] Patent Number: 5,099,040

[45] Date of Patent: Mar. 24, 1992

[54] PROCESS FOR THE PREPARATION OF INTERMEDIATES

[75] Inventors: Winfried Rosen, Wuppertal; Paul-Christian Fiedler, Cologne; Götz Blume, Holzminden, all of Fed. Rep. of Germany

[73] Assignee: Bayer Aktiengesellschaft, Leverkusen, Fed. Rep. of Germany

[21] Appl. No.: 749,035

[22] Filed: Aug. 23, 1991

[30] Foreign Application Priority Data

Aug. 31, 1990 [DE] Fed. Rep. of Germany ....... 4027608

[51] Int. Cl.⁵ ................. C07D 301/02; C07D 301/26; C07C 29/40; C07C 33/50
[52] U.S. Cl. ..................................... 549/519; 568/807
[58] Field of Search .................. 549/521, 519; 568/807

[56] References Cited

U.S. PATENT DOCUMENTS

| | | | |
|---|---|---|---|
| 3,388,179 | 6/1968 | Ramsden | 260/665 |
| 3,489,756 | 1/1970 | Bolhofer et al. | 549/519 |
| 4,301,166 | 11/1981 | Regel et al. | 568/807 |
| 4,416,682 | 11/1983 | Worthington | 568/807 |
| 4,898,954 | 2/1990 | Mohrmann et al. | 549/519 |
| 4,913,727 | 4/1990 | Stroech et al. | 71/92 |
| 4,929,735 | 5/1990 | Reiser et al. | 549/519 |
| 4,960,911 | 10/1990 | Zerbes et al. | 549/519 |
| 4,973,767 | 11/1990 | Crowley et al. | 568/807 |

Primary Examiner—J. E. Evans
Attorney, Agent, or Firm—Sprung Horn Kramer & Woods

[57] ABSTRACT

A new process for the preparation of 1-chloro-2-(1-chloro-cyclopropyl)-3-(2-chloro-phenyl)-propan-2-ol of the formula

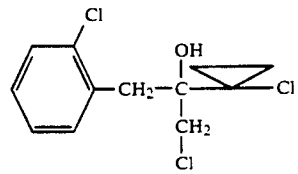

and/or 2-(1-chloro-cyclopropyl)-2-(2-chloro-benzyl)-oxirane of the formula

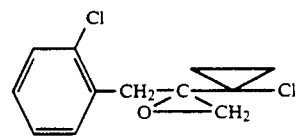

comprising
a) reacting in a first step, 2-chloro-benzyl chloride of the formula

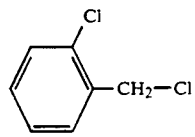

with comminuted magnesium in the presence of a mixture of toluene and tetrahydrofuran, in which the ratio of toluene to tetrahydrofuran is between 65:35 and 95:5 parts by weight, at a temperature between 0° C. and 100° C., the ratio of 2-chloro-benzyl chloride to tetrahydrofuran being such that between 1 and 3 moles of tetrahydrofuran are present per mol of 2-chloro-benzyl chloride, and subsequently separating off any magnesium which may still be present, and
b) reacting the resulting Grignard reagent of the formula (Abstract continued on next page.)

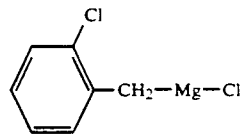
in a second step with 1-chloro-1-chloroacetylcyclopropane of the formula
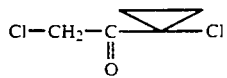
in the presence of a mixture of toluene and tetrahydrofuran, in which the ratio of toluene to tetrahydrofuran is between 65:35 and 95:5 parts by weight, at a temperature between 0° C. and 100° C.
10 Claims, 1 Drawing Sheet

PROCESS FOR THE PREPARATION OF INTERMEDIATES

The present invention relates to a new process for the preparation of 1-chloro-2-(1-chloro-cyclopropyl)3-(2-chloro-phenyl)-propan-2-ol and/or 2-(1-chlorocyclopropyl)-b 2-(2-chloro-benzyl)-oxirane, which can be used as intermediates for the synthesis of 2-(1-chlorocyclopropyl)-1-(2-chloro-phenyl)-3-(1,2,4-triazol-1-yl)propan-2-ol, which is fungicidally active.

It has already been disclosed that certain cyclopropylhydrins and cyclopropyl-oxiranes which are suitable as intermediates for the synthesis of azolyl derivatives, can be prepared by reacting benzyl Grignard compounds with halogenoacetyl-cyclopropyl derivatives (cf. EP-OS (European Published Specification) 0,297,345. For example, 1-chloro-2-(1-chloro-cyclopropyl)-3-(4-fluorophenyl)-propan-2-ol can be obtained by reacting 4-fluorobenzyl bromide with magnesium flakes in the presence of diethyl ether, and allowing the resulting Grignard compound to further react with 1-chloro-1-chloroacetylcyclopropane in the presence of diethyl ether. However, the disadvantage of this process is the fact that such a reaction in diethyl ether as the diluent is extremely difficult to carry out on an industrial scale, for safety reasons.

Furthermore, it has already been disclosed that organomagnesium compounds can be prepared in some cases in the presence of ethers, such as tetrahydrofuran, and aromatic hydrocarbons, such as toluene, or their mixtures as diluents (cf. U.S. Patent Specification 3,388,179). However, a broad range of application of this method has not been described to date.

It has now been found that 1-chloro-2-chloro-cyclopropyl)-3-(2-chloro-phenyl)-propan-2-ol, of the formula

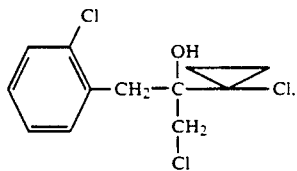

and/or 2-(1-chloro-cyclopropyl)-2-(2-chloro-benzyl)oxirane, of the formula

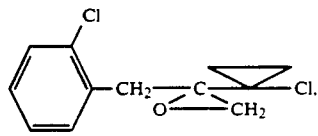

are obtained when
a) 2-chloro-benzyl chloride, of the formula

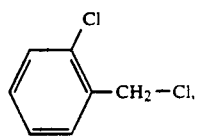

is reacted with comminuted magnesium, if appropriate in the presence of a catalyst, in the presence of a mixture of toluene and tetrahydrofuran, in which the ratio of toluene to tetrahydrofuran is between 65:35 and 95:5 parts by weight, at temperatures between 0° C. and 100° C., the ratio of 2-chloro-benzyl chloride, of the formula (II), to tetrahydrofuran being such that between 1 and 3 moles of tetrahydrofuran are present per mol of 2-chloro-benzyl chloride, of the formula (II), any magnesium which may still be present is subsequently separated off, and b) the resulting Grignard reagent of the formula

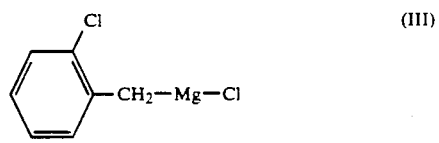

is reacted with 1-chloro-1-chloroacetylcyclopropane, of the formula

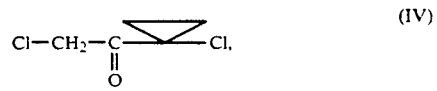

in the presence of a mixture of toluene and tetrahydrofuran, in which the ratio of toluene to tetrahydrofuran is between 65:35 and 95:5 parts by weight, and, if appropriate, in the presence of an additional inert diluent, at temperatures between 0° C. and 100° C.

It must be regarded as extremely surprising that the intermediates of the formulae (Ia) and (Ib) can be prepared in a very high yield by the process according to the invention, while they are only obtained in poor yields when the reaction is carried out in the presence of tetrahydrofuran as the only diluent, or of other ethers which can be used in industry, or in the presence of those toluene/tetrahydrofuran mixtures which contain only a little toluene. The fact that the desired products are formed in considerably better yield when 2-chloro-benzyl chloride, of the formula (II), is used instead of the corresponding 2-chloro-benzyl bromide, is also unexpected.

The process according to the invention is distinguished by a series of advantages. For example, the Grignard reaction, in which certain mixtures of toluene and tetrahydrofuran act as the diluent, can also be carried out on an industrial scale without difficulty. Moreover, it is advantageous that the desired products are obtained in very high yields and good purity. Another advantage of the process according to the invention consists in the fact that it can be carried out not only batchwise, but also continuously.

The course of the process according to the invention can be illustrated by the following equation:

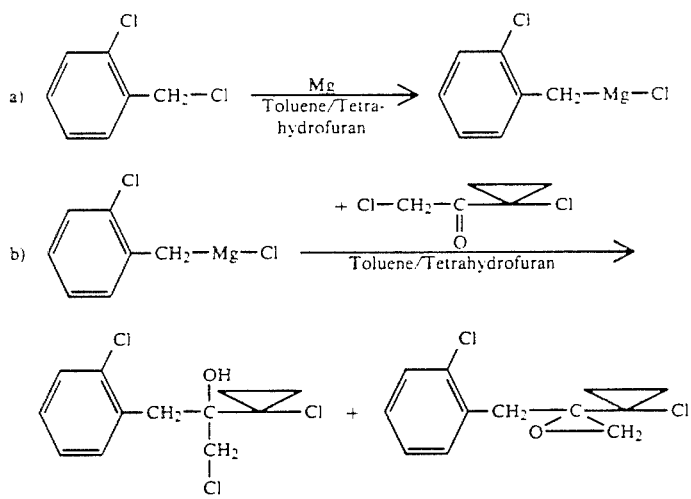

2-Chloro-benzyl chloride, of the formula (II), which is required as starting substance for carrying out the process according to the invention, is known.

1-Chloro-1-chloroacetyl-cyclopropane, of the formula (IV), which is required as the reactant for carrying out the second step of the process according to the invention, is also known (cf. EP-OS (European Published Specification) 0.297,345).

When carrying out the first step of the process according to the invention, the magnesium is employed in comminuted form. Magnesium flakes or magnesium powder can preferably be used.

Suitable catalysts for carrying out the first step of the process according to the invention are all reaction accelerators which are customary for such Grignard reactions. Iodine can preferably be used.

The diluent used for carrying out the first step of the process according to the invention is a mixture of toluene and tetrahydrofuran, in which the ratio of toluene to tetrahydrofuran is between 65:35 and 95:5, preferably between 70:30 and 90:10, parts by weight.

The second step of the process according to the invention is carried out advantageously in the presence of the same diluent is also used for carrying out the first step. The diluent employed is therefore generally a mixture of toluene and tetrahydrofuran, in which the ratio of toluene to tetrahydrofuran is between 65:35 and 95:5, preferably between 70:30 and 90:10, parts by weight. However, it is also possible to replace the mixture of toluene and tetrahydrofuran completely or partially by other inert diluents. Suitable diluents of this type are inert organic solvents such as aliphatic, alicyclic and aromatic hydrocarbons. The following may be mentioned by way of example: pentane, hexane, heptane, cyclohexane, methylcyclohexane, xylene and benzene, and mixtures of these solvents.

When carrying out the process according to the invention, the reaction temperatures can be varied within a substantial range, in the first step as well as in the second step. The first step is generally carried out at temperatures between 0° C. and 100° C., preferably between 20° C. and 50° C. The second step is generally carried out at temperatures between 0° C. and 100° C., preferably between 0° C. and 30° C.

In the case of the process according to the invention, the reaction times can also be varied within a substantial range when carrying out the first as well as the second step. They generally depend on the quantity of the substances to be reacted.

The process according to the invention is generally carried out under atmospheric pressure. However, it is also possible to carry out the process under reduced or increased pressure.

When carrying out the first step of the process according to the invention, 2-chloro-benzyl chloride, of the formula (II), is reacted with an equivalent amount or, alternatively, with an excess of magnesium and, if appropriate, with a very small amount of catalyst, in the presence of a mixture of toluene and tetrahydrofuran. The amounts in this context should be such that between 1 and 5 moles, preferably between 1.05 and 3 moles, of magnesium, between 1 and 3 moles, preferably between 1.5 and 2.5 moles, of tetrahydrofuran and, if appropriate, between 0.001 and 0.008 mole, of catalyst are present per mole of 2-chloro-benzyl chloride, of the formula (II).

When carrying out the second step of the process according to the invention, the ratio of the reactants can also be varied within a certain range. In this context, the proportions are chosen such that between 1 and 2.5 moles, preferably between 1.1 and 1.7 moles, of Grignard compound of the formula (III) are generally present per mol of 1-chloro-1-chloroacetyl-cyclopropane of the formula (IV).

Excess magnesium which may be present is separated off by customary methods when the first step has ended. For example, the magnesium can be removed by filtration or centrifugation, or by decanting off, or pumping off, the supernatant solution after the magnesium has settled.

When carrying out the process according to the invention, a specific procedure is followed in which comminuted magnesium mixed with a small amount of diluent and, if appropriate, mixed with the catalyst, is initially introduced, a little 2-chloro-benzyl chloride is then added, and, once the reaction has started up, the remainder of the 2-chloro-benzyl chloride, mixed with diluent, is slowly added dropwise. When the reaction has ended, any excess magnesium which may be present is removed, and 1-chloro-1-chloroacetyl-cyclopropane and, if appropriate, additional diluent are then added to the Grignard solution. The mixture is subsequently worked up by customary methods. In general, a procedure is followed in which the reaction mixture is either poured into a cooled mixture of water and acid or poured into cooled water, and the mixture is then rendered neutral or weakly acidic by adding acid, and the organic phase is subsequently separated off, washed with water and then concentrated. However, the mixture can also be worked up in such a way that, when the reaction has ended, it is first heated to temperatures between 30° C. and 100° C. and then cooled, the solid obtained in this process is filtered off with suction, and the filtrate is concentrated. If appropriate, the product obtained after the particular working-up procedure can be further purified by customary methods.

In a particular variant, the Grignard reaction of the process according to the invention can be carried out in a fluidised bed. For this purpose, the reaction can be carried out in an apparatus as is shown in FIG. 1 in the form of a diagram. In this figure, the numbers indicated have the following meanings:

1 = reaction tube
2 = sieve at the inlet of the reaction tube
3 = sieve at the outlet of the reaction tube
4 = lower filling level
5 = upper filling level
6 = storage container
7 = pump
8 = valve
9 = storage container
10 = feedpipe
11 = measurement point for temperature
12 = measurement point for temperature
13 = reaction vessel
14 = storage container
15 = heat exchanger
16 = heat exchanger For carrying out the process according to the invention in a fluidised-bed circulation reactor of the type outlined in FIG. 1, a procedure as described below is generally followed:

The reaction tube 1, at whose inlet 2 and outlet 3 there is arranged a sieve in each case, is charged with comminuted magnesium up to filling level 4. To facilitate starting-up of the Grignard reaction, a small amount of catalyst is placed on the surface of the magnesium when the first batch is carried out. With the aid of pump 7, a mixture of toluene and tetrahydrofuran is then slowly pumped from storage container 6 via valve 8 into reaction tube 1, until the surface of the liquid reaches filling level 4. With a pipette, a small amount of mixture is removed from storage container 9, which contains a mixture of toluene, tetrahydrofuran and 2-chlorobenzyl chloride, and this mixture is fed to reaction tube 1 via feedpipe 10 in order to start the Grignard reaction. Once the reaction has started up, the flow rate of the solvent mixture from storage container 6 through valve 8 is adjusted in such a way that the magnesium in reaction tube 1 is whirled up to level 5. Metering in of the mixture from storage container 9 is started simultaneously. With the aid of heat exchanger 15, the temperature of the recirculating mixture is controlled in such a way that it is at the desired reaction temperature at measurement point 11. At measurement point 12, the value is in each case approximately 1° C. higher. When the addition of the mixture from storage container 9 has ended, the mixture is allowed to after-react for some time with further recirculation, and the entire liquid content is then allowed to pass from the apparatus into reaction vessel 13. To this mixture 1-chloro-1-chloroacetyl-cyclopropane from storage container 14 is added dropwise with cooling and stirring. When the addition has ended, stirring is continued for some time, and the mixture is then worked up by hydrolysation with a mixture of water and acid, separation of the phases and concentration of the organic phase.

In all the following batches, which are carried out in the fluidised-bed circulation reactor, the addition of more catalyst can be dispensed with. The magnesium which has been consumed is replaced in each case.

The reaction in the fluidised bed can either be carried out batchwise or, alternatively, continuously.

When carrying out the process according to the invention, 1-chloro-2-(1-chloro-cyclopropyl)-3-(2-chlorophenyl)propan-2-ol, of the formula (Ia), and/or 2-(1-chlorocyclopropyl)-2-(2-chloro-benzyl)-oxirane, of the formula (Ib), is formed. The substance of the formula (Ia) is generally present in a higher proportion than the compound of the formula (Ib). However, 1-chloro2-(1-chloro-cyclopropyl)-3-(2-chloro-phenyl)-propan-2-ol, of the formula (Ia), can be converted into 2-(1-chloro-cyclopropyl)-2-(2-chloro-benzyl)-oxirane, of the formula (Ib), by elimination of hydrogen halide, for example thermally or with the aid of bases.

The products of 1-chloro-2-(1-chloro-cyclopropyl)-3-(2-chloro-phenyl)-propan-2-ol, of the formula (Ia), and/or 2-(1-chloro-cyclopropyl)-2-(2-chloro-benzyl)oxirane, of the formula (Ib), which can be prepared by the process according to the invention, are valuable intermediates for preparing 2-(1-chloro-cyclopropyl)-1-(2-chlorophenyl)-3-(1,2,4-triazol-1-yl)-propan-2-ol, which is fungicidally active. Thus 2-(1-chloro-cyclopropyl)-1-(2-chloro-phenyl)-3-(1,2,4-triazol-1-yl)propane-2-ol, of the formula

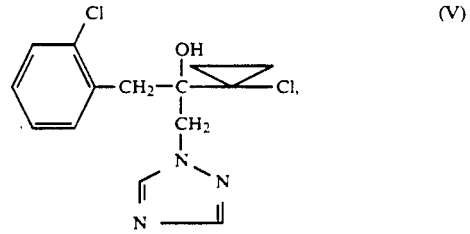

(V)

can be prepared by reacting either 1-chloro-2-(1-chlorocyclopropyl)-3-(2-chloro-phenyl)-propan-2-ol, of the formula

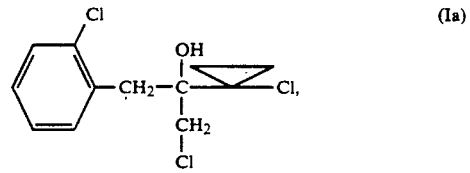

(Ia)

or 2-(1-chloro-cyclopropyl)-2-(2-chloro-benzyl)-oxirane, of the formula

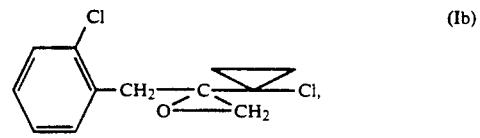

(Ib)

or a mixture of the substances of the formulae (Ia) and (Ib), with 1,2,4-triazole, of the formula

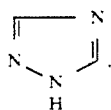

in the presence of an acid-binding agent and in the presence of a diluent, at temperatures between 0° C. and 150° C.

The examples which follow illustrate how the process according to the invention is carried out.

PREPARATION EXAMPLES

EXAMPLE 1

A mixture of 17 g (0.7 mol) of magnesium flakes and 0.1 g of iodine is treated with 42 g of toluene, 8 g of tetrahydrofuran and 1 g of 2-chloro-benzyl chloride, at 20° C. Once the reaction has started up, a mixture of 97 g (0.61 mol in total) of 2-chloro-benzyl chloride, 338 g of toluene and 67 g of tetrahydrofuran is added dropwise in the course of 5 hours at temperatures between 50 and 55° C. When the addition has ended, the mixture is allowed to after-react for a further 30 minutes at 50° to 55° C., and the reaction mixture is then cooled to 20° C., and unreacted magnesium is removed by decanting. Into the decanted reaction mixture 87 g (0.54 mol) of 1-chloro-1-chloroacetyl-cyclopropane are added dropwise in the course of 45 minutes at temperatures between 20° and 30° C. When the addition has ended, the mixture is allowed to after-react for a further 30 minutes at 20° to 30° C., and the reaction mixture is then poured into a solution of 24 g of concentrated sulphuric acid in 170 g of water in the course of 30 minutes at temperatures between 0° C. and 20° C. The organic phase is separated off, washed twice using 100 g portions of water, and then concentrated under reduced pressure at 80° C. In this manner, 156 g of a product are obtained of which 44.2% is 1-chloro-2-(1-chloro-cyclopropyl)-3-(2-chloro-phenyl)-propan-2-ol and 30.4% is 2-(1-chloro-cyclopropyl)-2-(2-chloroirane. benzyl)-oxirane. Accordingly, the yield relative to 1-chloro-1-chloroacetylcyclopropane employed is calculated as 81.8% of theory.

EXAMPLE 2

A mixture of 34 g (1.4 mol) of magnesium flakes and 0.1 g of iodine is treated at 20° C. with 26 g of toluene, 1 g of tetrahydrofuran and 1 g of 2-chloro-benzyl chloride. After the reaction has started up, a mixture of 97 g (0.61 mol in total) of 2-chloro-benzyl chloride and 67 g of tetrahydrofuran is added dropwise in the course of 4.5 hours at temperatures between 40° and 45° C. During the first 15 minutes of the addition, 158 g of toluene are simultaneously added in such a way that the heat of the reaction is utilised for warming the solvent. When the addition has ended, the mixture is allowed to after-react for a further 30 minutes at 40° to 45° C., the reaction mixture is then cooled to 20° C., and unreacted magnesium is removed by decanting. To the decanted reaction mixture 78 g (0.48 mol) of 1-chloro-1-chloroacetyl--cyclopropane are added dropwise in the course of 60 minutes, at temperatures between 20° and 30° C. When the addition has ended, the mixture is allowed to after-react for a further 30 minutes at 20° to 25° C., and working-up is effected by first refluxing the reaction mixture for 1 hour and then cooling it to 20° C. and filtering off the precipitated solid with suction. The filtrate is concentrated under reduced pressure at 80° C. In this manner, 138 g of a product are obtained, of which 68.4% is 2-(1-chloro-cyclopropyl)-2-(2-chloro-benzyl)-oxirane. Accordingly, the yield relative to 1-chloro-1-chloroacetyl-cyclopropane employed is calculated as 80.9% of theory.

EXAMPLE 3

A mixture of 68 g (2.8 mol) of magnesium flakes and 0.1 g of iodine is treated with 26 g of toluene, 1 g of tetrahydrofuran and 1 g of 2-chloro-benzyl chloride, at 20° C. When the reaction has started up, a mixture of 97 g (0.61 mol in total) of 2-chloro-benzyl chloride and 69 g of tetrahydrofuran is added dropwise at temperatures between 40° and 45° C. in the course of 4.5 hours. During the first 15 minutes of the addition, 154 g of toluene are simultaneously added in such a way that the heat of the reaction is utilised for warming the solvent. When the addition has ended, the mixture is allowed to after-react for a further 30 minutes at 40° to 45° C., and the reaction mixture is then cooled to 20° C., and unreacted magnesium is removed by decanting. To the decanted reaction mixture 61 g (0.375 mol) of 1-chloro-1-chloroacetyl-cyclopropane are added dropwise in the course of 60 minutes at temperatures between 20° and 25° C. When the addition has ended, the mixture is allowed to after-react for a further 30 minutes at 20° to 25° C., and the reaction mixture is then poured into a solution of 24 g of concentrated sulphuric acid in 170 g of water, in the course of 30 minutes, at temperatures between 0° C. and 10° C. The organic phase is separated off, washed twice with 100 g portions of water and then concentrated under reduced pressure at 70° to 75° C. In this manner, 130 g of a product are obtained, of which 55.1% is 1-chloro-2-(1-chloro-cyclopropyl)-3-(2-chloro-benzyl) -propan-2-ol and 15.8% is 2-(1-chlorocyclopropyl)-2-(2-chloro-benzyl)-oxirane. Accordingly, the yield relative to 1-chloro-1-chloroacetyl-cyclopropane employed is calculated at 90.8% of theory.

EXAMPLE 4

A mixture of 190 g (7.8 mol) of magnesium flakes and 0.5 g of iodine is treated with 200 g of toluene, 10 g of tetrahydrofuran and 3 g of 2-chloro-benzyl chloride, at 20° C. When the reaction has started up, a mixture of 1160 g (7.2 mol in total) of 2-chloro-benzyl chloride and 881 g of tetrahydrofuran is added dropwise at temperatures between 40° and 45° C. in the course of 5 hours. During the first 30 minutes of the addition, 2,200 g of toluene are simultaneously added in such a manner that the heat of reaction is utilised for heating the solvent. When the addition has ended, the mixture is allowed to after-react for a further 30 minutes at 40° to 45° C., and the reaction mixture is then cooled to 20° C., and unreacted magnesium is removed by decanting. To the decanted reaction mixture 965 g (6 mol) of 1-chloro-1-chloroacetyl-cyclopropane are added dropwise in the course of 1 hour at temperatures between 20 and 25° C. When the addition has ended, the mixture is allowed to after-react for 30 minutes at 20° to 25° C., and the reaction mixture is then poured into a solution of 150 g of concentrated sulphuric acid in 1700 g of water, in the course of 30 minutes, at temperatures between 0° C. and 10° C. The organic phase is separated off, washed twice with 500 g portions of water and then concentrated under reduced pressure at 80° C. In this manner, 1750 g of a product are obtained of which 53.1% is 1-chloro-2-

(1-chloro-cyclopropyl)-3-(2-chloro-phenyl)-propan-2-ol and 22.8% is 2-(1-chloro-cyclopropyl)-2-(2-chlorobenzyl)oxirane. Accordingly, the yield relative to 1-chloro-1-chloroacetyl-cyclopropane employed is calculated as 82.7% of theory.

EXAMPLE 5

Grignard reaction of the process according to the invention, carried out in a fluidised-bed circulation reactor of the type outlined in FIG. 1.

Reaction tube 1 at whose inlet 2 and outlet 3 there is provided a sieve in each case is filled with 60 g of magnesium flakes (1-3 mm) to filling level 4. To facilitate the starting-up of the Grignard reaction, a spatulatip full of iodine is placed on the surface of the magnesium. Then a mixture of 750 g of toluene and 20 g of tetrahydrofuran is slowly pumped from storage container 6 via valve 8 into reaction tube 1, with the aid of pump 7, until the surface of the liquid has reached filling level 4. With a pipette, 5 ml of mixture are removed from storage container 9 which contains a mixture of 100 g of toluene, 130 g of tetrahydrofuran and 161 g of 2-chlorobenzyl chloride, and these 5 ml of mixture are fed into reaction tube 1 through feedpipe 10, so as to start the Grignard reaction. The starting-up of the Grignard reaction can be recognised by local heating and by the disappearance of the brown coloration which the iodine had caused. Once the reaction has started up, the flow rate of the solvent mixture from storage container 6 through valve 8 is adjusted in such a way that the magnesium in reaction tube 1 is whirled up to level 5 metering in of the mixture in storage container 9 is started simultaneously. The addition is carried out in the course of 5 hours. During this process, the temperature of the recirculating mixture is controlled with the aid of heat exchanger 15 in such a way that it is 35° to 37° C. at measurement point 11. The value at measurement point 12 is 1° C. higher. When the addition of the mixture from storage container 9 has ended, the mixture is allowed to after-react for a further 90 minutes with further recirculation, and the entire liquid content is then allowed to pass from the apparatus into reaction vessel 13. 100 g of 1-chloro-1-chloroacetyl-cyclopropane from storage container 14 are added dropwise in the course of 30 minutes at 10° to 15° C. with stirring. When the addition has ended, stirring is continued for a further 30 minutes at 20° C., and the mixture is then worked up by hydrolysis in a mixture of water and acetic acid. The organic phase is separated off and concentrated under reduced pressure. There remain 224 g of an oil which, according to gas chromatogram, contains 125.0 g of 1-chloro-2-(1-chloro-cyclopropyl)-3-(2-chloro-phenyl)-propan-2-ol and 10.9 g of 2-(1-chloro cyclopropyl)-2-(2-chloro-benzyl)-oxirane. Accordingly, the yield relative to 1-chloro-1-chloro-acetyl-cyclopropane employed is calculated as 82.3% of theory.

EXAMPLE 6

Grignard reaction of the process according to the invention, carried out in a continuously operating fluidisedbed circulation reactor.

The reaction tube in which there are 500 g of magnesium flakes between the sieves is filled with a mixture of 2-chlorobenzyl chloride, toluene and tetrahydrofuran of the desired composition. By means of a pump, the mixture is circulated at the flow rate of 200 litres per hour, so that the magnesium in the reaction tube is whirled up. By cooling with a heat exchanger, the temperature in the fluidised bed is kept constant at 35° C. Moreover, the reaction mixture in the entire apparatus is kept under nitrogen.

Using a metering pump, a mixture consisting of
13.7 percent by weight of 2-chloro-benzyl chloride,
12.7 percent by weight of tetrahydrofuran and
73.5 percent by weight of toluene is then continuously pumped in from below into the fluidised bed in the reaction tube, at a rate of 2.8 kg per hour. Simultaneously, a mixture containing the formed Grignard compound flows into a stirred reactor via an overflow at approximately the same rate of 2.8 kg per hour. The reaction tube is re-stocked with 57 g of magnesium flakes per hour, via a ball valve. 100 minutes after operation of the apparatus has started, there are 4.8 kg in the stirred reactor. The overflow is now shut while circulation of the mixture from the reaction tube in the apparatus continues with the aid of the metering pump. Grignard compound which is formed continuously in this process is passed into a further storage container and stored there until it is employed for further reaction in the stirred reactor which has then been emptied.

From an additional storage container, 510 g of 1-chloro-1-chloroacetyl-cyclopropane are metered into the stirred reactor in which there is the Grignard compound as a mixture with toluene and tetrahydrofuran, in the course of 30 minutes at 20 to 25° C. When the addition has ended, stirring of the reaction mixture is continued at 20 to 25° C. for a further 15 minutes and the mixture is then drained off and collected in a separate vessel until it is worked up. The overflow is then re-opened so that the stirred reactor is again provided with Grignard compound. Moreover, the Grignard compound stored in the storage container is also passed into the stirred reactor, so that a further reaction with 1-chloro-1-chloroacetylcyclopropane takes place therein.

For working-up, the reaction mixture is treated with a mixture of concentrated sulphuric acid and water. The organic phase is separated off and concentrated under reduced pressure at increased temperature. During this process, there remain 20 g of an oil which, according to gas chromatogram, consists of 16.9% of 1-chloro-2-(1-chloro-cyclopropyl)-3-(2-chloro-phenyl)-propan-2-ol and 52.4% of 2-(1-chloro-cyclopropyl)-2-(2-chloro-benzyl)-oxirane. Accordingly, the yield relative to 1-chloro-1-chloroacetyl-cyclopropane employed is calculated as 92.1% of theory.

COMPARISON EXAMPLE 1

Use of methyl tert.-butyl ether as the diluent.

A mixture of 7 g (0.29 mol) of magnesium flakes, 40 g of methyl tert.-butyl ether and 0.1 g of iodine is treated at 20° C. with 3 g of 2-chloro-benzyl chloride and then heated to 30° C. When the reaction has started up, a further 80 g of methyl tert.-butyl ether are first added. Then a solution of 42 g (0.28 mol in total) of 2-chlorobenzyl chloride in 80 g of methyl tert.-butyl ether is added dropwise at 50° C. in the course of 3 hours. When the addition has ended, the reaction mixture is allowed to after-react for a further hour at 50° C. and then cooled to 20° C., and unreacted magnesium is removed by decanting. This decanted reaction mixture is added to a solution of 25 g (0.155 mol) of 1-chloro-1-chloroacetyl-cyclopropane in 40 g of methyl tert.-butyl ether in the course of 1 hour, with stirring. When the addition has ended, the reaction mixture is stirred for a further 3 hours at 20° C., treated with ice-water and rendered neutral using dilute sulphuric acid.

The organic phase is separated off, washed twice with 100 g portions of water and then concentrated at 70° C. under reduced pressure. In this manner, 53.4 g of a product are obtained which consists of 40.3% of 1-chloro-2-(1-chloro-cyclopropyl)-3-(2-chloro-phenyl)-propan-2-ol. Accordingly, the yield relative to 1-chloro-1-chloroacetyl-cyclopropane employed is calculated as 50.1% of theory.

COMPARISON EXAMPLE 2

Use of methyl tert.-amyl ether as the diluent.

A mixture of 40 g (1.65 mol) of magnesium flakes, 85 g of methyl tert.-amyl ether and 0.1 g of iodine is treated at 20° C. with 5 g of 2-chloro-benzyl chloride and then heated to 60° C. When the reaction has started up, a further 700 g of methyl tert.-amyl ether are first added. Then 196 g (1.25 mol in total) of 2-chloro-benzyl chloride are added dropwise at temperatures between 65° and 70° C. in the course of 4 hours. 195 g (1.2 mol) of 1-chloro-1-chloroacetyl-cyclopropane are subsequently added dropwise at 45 to 50° C. in the course of 2 hours. When the addition has ended, the reaction mixture is stirred for a further 2 hours at 30° to 35° C. and then treated with 350 g of water and 80 g of acetic acid at 5° to 10° C. in the course of one hour. The organic phase is separated off, washed with 200 g of water and then concentrated at 70° C. under reduced pressure. In this manner, 350 g of a product are obtained which consists of 51.5% of 1-chloro-2-(1-chlorocyclopropyl)-3-(2-chloro-phenyl)-propan-2-ol. Accordingly, the yield relative to 1-chloro-1-chloroacetyl-cyclopropane employed is calculated as 53.7% of theory.

COMPARISON EXAMPLE 3

Use of 2-chloro-benzyl bromide for the preparation of the Grignard component.

A mixture of 17 g (0.7 mol) of magnesium flakes and 0.1 g of iodine is treated at 20° C. with 40 g of toluene and with 4 g of a mixture which had been obtained from 75 g of tetrahydrofuran and 127 g (0.6 mol) of 2-chloro-benzyl bromide. When the reaction has started up, the remaining 198 g of the mixture of tetrahydrofuran and 2-chloro-benzyl bromide are added dropwise in the course of 4 hours, during which process the temperature of the reaction mixture is maintained between 35° and 45° C. During the first 15 minutes of the addition, 140 g of toluene are simultaneously added in such a manner that the heat of reaction is utilised for heating the solvent. When the addition has ended, the mixture is allowed to after-react for a further 30 minutes at 40° to 45° C., the reaction mixture is then cooled to 20° C., and unreacted magnesium is removed by decanting. To the decanted reaction mixture 82 g (0.5 mol) of 1-chloro-1-chloro-acetyl-cyclopropane are added dropwise in the course of 1.5 hours at temperatures between 10° and 20° C. When the addition has ended, the reaction mixture is allowed to after-react for a further 30 minutes at 20° to 30° C. and is then added to a solution of 15 g of concentrated sulphuric acid in 200 g of water, in the course of 30 minutes at temperatures between 0° C. and 20° C. The organic phase is separated off, washed twice with 100 g portions of water and then concentrated at 80° C. under reduced pressure. In this manner, there are obtained 162 g of a product which consists of 38.9% of 1-chloro-2-(1-chloro-cyclopropyl)-3-(2-chloro-phenyl)-propan-2-ol and of 13.5% of 2-(1-chloro-cyclopropyl)-2-(2-chloro-benzyl)-oxirane. Accordingly, the yield relative to 1-chloro-1-chloroacetyl-cyclopropane employed is calculated as 62.9% of theory.

COMPARISON EXAMPLE 4

Use of a diluent which consists of equal parts of toluene and tetrahydrofuran.

A mixture of 17 g (0.7 mol) of magnesium flakes and 0.1 g of iodine is treated at 20° C. with 10 g of toluene, 10 g of tetrahydrofuran and 1 g of 2-chloro-benzyl chloride. When the reaction has started up, a mixture of 97 g (0.61 mol in total) of 2-chloro-benzyl chloride, 240 g of toluene and 240 g of tetrahydrofuran is added dropwise at temperatures between 35° and 45° C. in the course of 5 hours. When the addition has ended, the reaction mixture is allowed to after-react for a further 30 minutes at 30 to 40° C. and is then cooled to 20° C., and unreacted magnesium is removed by decanting. To the decanted reaction mixture 87 g (0.54 mol) of 1-chloro-1-chloro-acetyl-cyclopropane are added dropwise in the course of 40 minutes at temperatures between 20° and 30° C. When the addition has ended, the reaction mixture is allowed to after-react for a further 30 minutes at 30° to 35° C. and is then added to a solution of 30 g of glacial acetic acid in 120 g of water, in the course of 30 minutes at temperatures between 0° C. and 10° C. The organic phase is separated off, washed with 100 g of water and then concentrated at 70° C. under reduced pressure.

In this manner, there are obtained 166 g of a product which consists of 5.6% of 1-chloro-2-(1-chloro-cyclopropyl)-3-(2-chloro-phenyl)-propan-2-ol and 2.4% of 2-(1-chloro-cyclopropyl)-2-(2-chloro-benzyl)-oxirane. Accordingly, the yield relative to 1-chloro-1-chloroacetyl-cyclopropane employed is calculated as 9.2% of theory.

COMPARISON EXAMPLE 5

Use of tetrahydrofuran as the only diluent.

A mixture of 17 g (0.7 mol) of magnesium flakes and 0.1 g of iodine is treated at 20° C. with 20 g of tetrahydrofuran and 1 g of 2-chloro-benzyl chloride. When the reaction has started up, a solution of 97 g (0.61 mol in total) of 2-chlorobenzyl chloride in 250 g of tetrahydrofuran is added dropwise at temperatures between 40° and 45° C. in the course of 4 hours. When the addition has ended, the reaction mixture is allowed to after-react for a further hour at 30° to 40° C. and is then cooled to 20° C., and unreacted magnesium is removed by decanting. To the decanted reaction mixture 10 g (0.06 mol) of 1-chloro-1-chloroacetyl-cyclopropane are added dropwise in the course of 30 minutes at temperatures between 20° to 25° C. When the addition has ended, the mixture is allowed to after-react for a further 30 minutes at 20° to 30° C., and a solution of 30 g of concentrated sulphuric acid in 150 g of water is then added dropwise to the reaction mixture in the course of 30 minutes at 0° C. to 10° C. The mixture is extracted by shaking with 170 g of toluene at 20° C., and the organic phase is concentrated at 70° C. under reduced pressure. In this manner, there are obtained 82 g of a product which contains less than 1% of 1-chloro-2-(1-chloro-cyclopropyl)-3-(2-chloro-phenyl)-propan-2-ol and 2-(1-chloro-cyclopropyl)-2-(2-chloro-benzyl)-oxirane.

USE EXAMPLE

Preparation of the compound of the formula

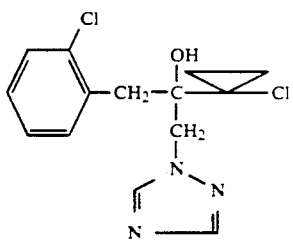

A solution of 218 g of a mixture which consists of 53.8% (0.42 mol) of 1-chloro-2-(1-chloro-cyclopropyl)-3-(2-chloro-phenyl)-propan-2-ol and 8.9% (0.08 mol) of 2-(1-chloro-cyclopropyl)-2-(2-chloro-benzyl)-oxirane in 160 g of methanol is treated at 20° C. with 45 g (0.65 mol) of 1,2,4-triazole. 138 g (1 mol) of anhydrous potassium carbonate is then added at temperatures between 30 and 35° C. in the course of one hour. The reaction mixture is subsequently heated to 70° C. and allowed to react at this temperature for 4.5 hours. The reaction mixture is cooled to 20° C. and treated with 500 g of water, with stirring. After 30 minutes, the upper aqueous phase is decanted off, and the residue is taken up in 150 g of methylene chloride and 250 g of water. The mixture is stirred for 15 minutes at 20° C., the solid which has precipiated is filtered off with suction and washed with 75 g of methylene chloride. After the aqueous phase has been separated off, the filtrate is concentrated at 80° C. under reduced pressure. The residue which remains is taken up in a mixture of 165 g of petroleum ether and 25 g of isopropanol. The mixture is heated to 60° C. until a clear solution has formed and is then cooled slowly to 10° C. in the course of 2 hours. The solid which crystallises out in this process is filtered off with suction, washed with a cooled mixture of 70 g of petroleum ether and 15 g of isopropanol, and dried at 50° C. under reduced pressure. In this manner, there are obtained 92 g of a product which consists of 96.3% of 2-(1-chloro-cyclopropyl)-1-(2-chloro-phenyl)-3-(1,2,4-triazol-1-yl)-propan-2-ol. Accordingly, the yield is calculated as 56.8% of theory.

It is understood that the specification and examples are illustrative but not limitative of the present invention and that other embodiments within the spirit and scope of the invention will suggest themselves to those skilled in the art.

What is claimed is:

1. A process for the preparation of 1-chloro-2-(1-chloro-cyclopropyl)-3-(2-chloro-phenyl)propan-2-ol of the formula

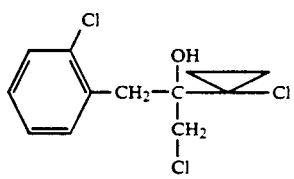

and/or 2-(1-chloro-cyclopropyl)-2-(2-chloro-benzyl)oxirane of the formula

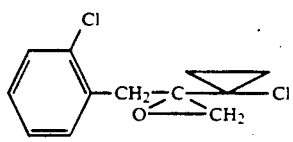

comprising a) reacting in a first step, 2-chloro-benzyl chloride of the formula

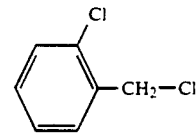

with comminuted magnesium int he presence of a mixture of toluene and tetrahydrofuran, in which the ratio of toluene to tetrahydrofuran is between 65:35 and 95:5 parts by weight, at a temperature between 0° C. and 100° c., the ratio of 2-chloro-benzyl chloride to tetrahydrofuran being such that between 1 and 3 moles of tetrahydrofuran are present per mol of 2-chloro-benzyl chloride, and subsequently separating off any magnesium which may still be present, and b) reacting the resulting Grignard reagent of the formula

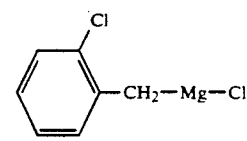

in a second step with 1-chloro-1-chloroacetylcyclopropane of the formula

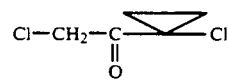

in the presence of a mixture of toluene and tetrahydrofuran, in which the ratio of toluene to tetrahydrofuran is between 65:35 and 95:5 parts by weight at a temperature between 0° C. and 100° C.

2. A process according to claim 1, wherein the first step of the reaction is carried out in the presence of a catalyst.

3. A process according to claim 2, wherein iodine is employed as the catalyst.

4. A process according to claim 1, wherein the comminuted magnesium is employed in the form of magnesium flakes.

5. A process according to claim 1, wherein a mixture of toluene and tetrahydrofuran is employed as the diluent when carrying out the first step, in which mixture the ratio of toluene to tetrahydrofuran is between 70:30 and 90:10 parts by weight.

6. A process according to claim 1, wherein the second step is carried out in the presence of an additional diluent.

7. A process according to claim 1, wherein the first step is carried out at a temperature between 20° C. and 50° C.

8. A process according to claim 1, wherein the second step is carried out at a temperature between 0° C. and 30° C.

9. A process according to claim 1, wherein between 1.5 and 2.5 moles of tetrahydrofuran are employed per mol of 2-chloro-benzyl chloride when carrying out the first step.

10. A process according to claim 1, wherein the first step is carried out in a fluidised bed.

* * * * *

: 
REEXAMINATION CERTIFICATE (1956th)

United States Patent [19]

Rosen et al.

[11] B1 5,099,040

[45] Certificate Issued Mar. 23, 1993

[54] PROCESS FOR THE PREPARATION OF INTERMEDIATES

[75] Inventors: Winfried Rosen, Wuppertal; Paul-Christian Fiedler, Cologne; Götz Blume, Holzminden, all of Fed. Rep. of Germany

[73] Assignee: Bayer Aktiengesellschaft, Leverkusen, Fed. Rep. of Germany

Reexamination Request:
No. 90/002,733, May 21, 1992

Reexamination Certificate for:
Patent No.: 5,099,040
Issued: Mar. 24, 1992
Appl. No.: 749,035
Filed: Aug. 23, 1991

[30] Foreign Application Priority Data

Aug. 31, 1990 [DE] Fed. Rep. of Germany ....... 4027608

[51] Int. Cl.$^5$ ................ C07D 301/02; C07D 301/26; C07C 29/40; C07C 33/50
[52] U.S. Cl. ............................. 549/519; 260/665 G; 568/807
[58] Field of Search ................. 549/519; 568/807; 260/665 G

[56] References Cited

U.S. PATENT DOCUMENTS

| | | | |
|---|---|---|---|
| 4,913,727 | 4/1990 | Stroech et al. | 71/92 |
| 5,099,040 | 3/1992 | Rosen et al. | 549/519 |

FOREIGN PATENT DOCUMENTS

| | | |
|---|---|---|
| 0047594 | 3/1982 | European Pat. Off. . |
| 0297345 | 1/1989 | European Pat. Off. . |
| 0415247 | 3/1991 | European Pat. Off. . |
| 2149087 | 4/1973 | Fed. Rep. of Germany . |
| 0870415 | 6/1961 | United Kingdom . |

OTHER PUBLICATIONS

Bulletin, Societe Chimique De France, 45, 1091–1095 (1929).
European Search Report (1991).

*Primary Examiner*—Joseph E. Evans

[57] ABSTRACT

A new process for the preparation of 1-chloro-2-(1-chloro-cyclopropyl)-3-(2-chloro-phenyl)-propan-2-ol of the formula

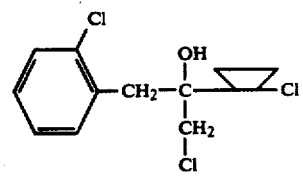

and/or 2-(1-chloro-cyclopropyl)-2-(2-chloro-benzyl)-oxirane of the formula

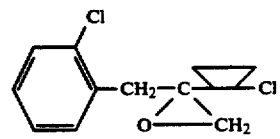

comprising
a) reacting in a first step, 2-chloro-benzyl chloride of the formula

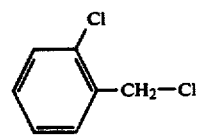

with comminuted magnesium in the presence of a mixture of toluene and tetrahydrofuran, in which the ratio of toluene to tetrahydrofuran is between 65:35 and 95:5 parts by weight, at a temperature between 0° C., and 100° C., the ratio of 2-chlorobenzyl chloride to tetrahydrofuran being such that between 1 and 3 moles of tetrahydrofuran are present per mol of 2-chloro-benzyl chloride, and subsequently separating off any magnesium which may still be present, and b) reacting the resulting Grignard reagent of the formula

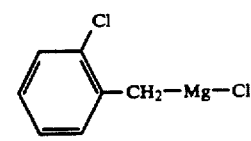

in a second step with 1-chloro-1-chloroacetylcyclopropane of the formula

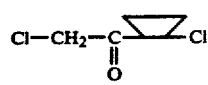

in the presence of a mixture of toluene and tetrahydrofuran, in which the ratio of toluene to tetrahydrofuran is between 65:35 and 95:5 parts by weight, at a temperature between 0° C. and 100° C.

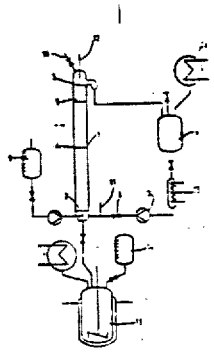

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 6 and 10 dependent on an amended claim, are determined to be patentable.

1. A process for the preparation of 1-chloro-2-(1-chloro-cyclopropyl)-3-(2-chloro-phenyl)propan-2-ol of the formula

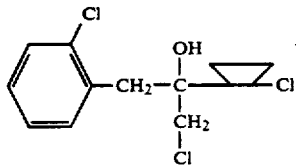

and/or 2-(1-chloro-cyclopropyl)-2-(2-chloro-benzyl)oxirane of the formula

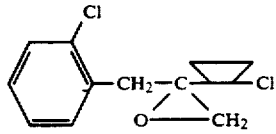

comprising
 a) reacting in a first step, 2-chloro-benzyl chloride of the formula

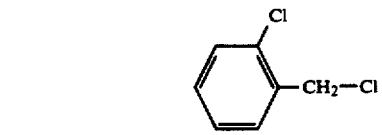

with comminuted magnesium in the presence of a mixture of toluene and tetrahydrofuran, in which the ratio of toluene to tetrahydrofuran is between [65.35 and 95:5] *70:30 and 90:10* parts by weight, at a temperature between [0° C., and 100° C.] *20° and 50° C.*, the ratio of 2-chloro-benzyl chloride to tetrahydrofuran being such that between [1 and 3] *1.5 and 2.5* moles of tetrahydrofuran are present per mol of 2-chloro-benzyl chloride, *the reaction being effected by adding a mixture of a major amount of the 2-chloro-benzyl chloride and the tetrahydrofuran to a mixture of magnesium flakes, iodine as catalyst, toluene and a minor amount of the 2-chloro-benzyl chloride and tetrahydrofuran;* and subsequently separating off any magnesium which may still be present, and
 b) reacting the resulting Grignard reagent of the formula

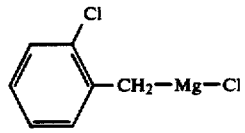

in a second step with 1-chloro-1-chloroacetylcyclopropane of the formula

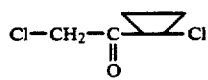

in the presence of a mixture of toluene and tetrahydrofuran, in which the ratio of toluene to tetrahydrofuran is between 63:35 and 95:5 parts by weight at a temperature between 0° C. and [100° C.] *30° C.*

* * * * *